United States Patent [19]

Perricone

[11] Patent Number: 5,709,868
[45] Date of Patent: Jan. 20, 1998

[54] LIPOIC ACID IN TOPICAL COMPOSITIONS

[76] Inventor: Nicholas V. Perricone, 27 Coginchaug Ct., Guilford, Conn. 06437

[21] Appl. No.: 531,290

[22] Filed: Sep. 20, 1995

[51] Int. Cl.$^6$ .................................. A61K 7/48; A61K 7/42
[52] U.S. Cl. .......................... 424/401; 424/59; 424/450; 514/785; 514/863; 514/887; 514/937; 514/944; 514/947; 514/969
[58] Field of Search .................... 424/401, 450, 424/59, DIG. 13; 514/944, 937, 969, 947, 886, 440, 887, 863, 785, 558

[56] References Cited

FOREIGN PATENT DOCUMENTS 63-008315  1/1988  Japan.

OTHER PUBLICATIONS

Maitra, I., et al., Free Rad. Biol. Med. 18:823–829 (1995).
Merck Index, 11th ed., 1989, Entry 9255 (p. 1469).

*Primary Examiner*—Thurman K. Page
*Attorney, Agent, or Firm*—St.Onge Steward Johnston & Reens

[57] ABSTRACT

In a method for the prevention and/or treatment of skin damage, particularly inflammation and aging, a composition containing lipoic acid and/or a lipoic acid derivative is topically applied to affected skin areas. A fat-soluble fatty acid ester of ascorbic acid such as palmityl ascorbate and/or tocotrienol is preferably applied with the lipoic acid or derivative in association with a dermatologically acceptable carrier.

15 Claims, No Drawings

LIPOIC ACID IN TOPICAL COMPOSITIONS

TECHNICAL FIELD

This invention relates to the topical application of compositions containing lipoic acid for the prevention and/or treatment of damage to skin, particularly for the treatment or prevention of inflammatory and aging effects from sunlight and chemical damage.

BACKGROUND OF THE INVENTION

Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. It has been variously known as acetate replacing factor, protogen A, and pyruvate oxidation factor.

Subsequent research showed that lipoic acid (LA) was a growth factor for many bacteria and protozoa and it served as a prosthetic group, coenzyme, or substrate in plants, microorganisms, and animal tissues. Elucidation of its structure and function determined that it is a co-factor for α-keto-dehydrogenase complexes, typically bound as lipoamide, that participates in acyl transfer reactions. Its reduced form, dihydrolipoic acid (DHLA), is a potent sulfhydryl reductant. In aqueous systems, both LA and DHLA exhibit antioxidant actions (briefly reviewed in the introduction of Maitra, I., et al., *Free Rad. Biol. Med.* 18:823–829 (1995)). LA has been shown to maintain microsomal protein thiols, protect against hemolysis, and protect against neurological disorders (ibid.). The protective effect of dietary supplementation of LA against ischemia/reperfusion injury in the Langendorff isolated heart model has also been demonstrated (ibid.). LA has been used in treating liver cirrhosis, atherosclerosis, and polyneuritis of diabetes mellitus, diseases in which oxidative stress plays a roll (ibid.). It has also been used as an antidote to poisonous mushrooms (particularly *Amanita* species, *Merck Index*, 11th ed., 1989, entry 9255).

The antioxidant activity of lipoic acid appears to prevent free radical damage to cells and cell components. Free radical damage is most evident in cellular membranes because of the density of the molecular structure of the membranes. It is currently hypothesized that cell membrane aging leads to all of the various cellular changes seen in aging, such as decreased RNA production, decreased protein production, and faulty enzyme action.

Inflammation in skin is mediated by several active chemicals and metabolites of arachidonic acid. Arachidonic acid is oxidized by cyclo-oxygenase and lipoxygenase to active metabolites such as the leukotrienes and 5- and 12- hydroxyeicosatetraenoic acid (HETES). Within the arachidonic acid cascade, many free radicals are generated, which both perpetuate and magnify the inflammatory cascade, resulting in skin damage and manifested clinically as erythema.

Early suggestions for dealing with erythema and aging effects in skin were predominantly aimed at lubrications and emollients through use of topical compositions containing soothing agents, e.g., as exemplified by commercial hand lotion products and the like. More recently, attention has been directed to agents which address the underlying processes involved in skin damage, such as the free radical generation processes. In this regard, investigations have been made with respect to the antioxidants vitamin E and vitamin C to quench free radicals on the surface of the skin and to protect lipid membranes intracellularly (Wilson, R., *Drug and Cosmetic Industry*, 32–34, 38, and 68, August 1992).

It would be desirable to have alternative topical compositions for anti-inflammatory and anti-aging effects observed in skin, particularly compositions that are efficient in free radical scavenging in membranes.

SUMMARY OF THE INVENTION

It is an object of this invention to provide a method and composition for the treatment and/or prevention of skin damage, particularly skin inflammation and aging mediated by free radicals.

It is another and more specific object of the invention to provide a topical composition and method for a preventive regimen and/or therapy based upon topical application to exposed or affected skin areas of an active agent or derivative thereof, in association with a dermatologically acceptable carrier or vehicle.

These and other objects are accomplished by the present invention, which provides a method for the prevention and/or treatment of skin inflammation, aging and other skin damage, which comprises topical application to the exposed or affected skin areas of an effective amount of lipoic acid, lipoic acid derivatives or mixtures thereof in a dermatologically acceptable carrier.

In many embodiments, tocotrienols or derivatives thereof or vitamin E compositions enriched with tocotrienols or tocotrienol derivatives are included in the lipoic acid composition. Ascorbic acid, particularly fat-soluble fatty acid esters of ascorbic acid such as ascorbyl palmitate, can, optionally, also be utilized for further enhancing the efficacy of the therapeutic or prophylactic treatment. Other reductants such as droxy acids and the like may also be added to the composition.

In one particularly preferred embodiment, the topical composition contains lipoic acid or dihydrolipoic acid or mixtures thereof, ascorbyl palmitate, and tocotrienol as active ingredients.

In the preferred practice of the invention, the lipoic acid (or derivative) is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas. As noted, other ingredients, particularly ascorbyl palmitate and/or tocotrienol, can be advantageously included in the compositions.

The amount of lipoic acid or derivative thereof (hereinafter referred to collectively as lipoic for ease of reference) necessary to bring about enhanced prevention and/or therapeutic treatment of skin damage is not fixed per se, and necessarily is dependent upon the identity and form of lipoic acid employed, the amount and type of any additional ingredients used, particularly those that appear to exhibit synergistic effects (to be discussed more fully below), the user's skin type, and, where present, the severity and extent of the patient's pathological skin or hair condition. Generally, the lipoic acid or composition containing it is topically applied in effective amounts to skin areas which have been damaged or aged, or which are susceptible to damage, because of inflammation or aging.

In one embodiment, the composition contains from about 0.25 to about 5 weight %, preferably from about 1% to about 3%, lipoic acid or dihydrolipoic acid. In one embodiment, 2% lipoic acid is employed.

DETAILED DESCRIPTION OF THE INVENTION

This invention is based upon the finding that lipoic acid and dihydrolipoic acid are useful for the treatment and prevention of damaged skin. Lipoic acid and its derivatives also augment the efficacy of other ingredients in topical compositions for inflammation, aging and other skin damage.

As used herein, the term "lipoic acid" encompasses thioctic acid (1,2-dithiolane-3-pentanoic acid; 1,2-dithiolane-3-valeric acid), which has the following general formula:

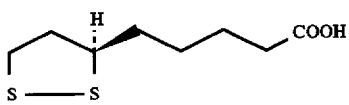

It is marketed under the tradenames Biletan™ by Gador Y Cia, Buenos Aires, Argentina; Lipoicin™ by Henkel A. G., Teaneck, N.J.; Thioctacid™ by Asta Medica, Hackensack, N.J.; Thioctan™ by Katwijk N.V., Amsterdam, Netherlands; Tioctan™ by Fujisawa Pharmaceutical Co., Ltd., Osaka, Japan; and Tioctidasi™ by ISI-Instituto Sierovaccinogno Italiano S.P.A., Antimo, Italy.

Lipoic acid derivatives include thioctic acid esters, particularly alkyl esters such as fatty acid esters, amides, particularly those isolated from or mimicking naturally occurring lipoamides, and salts, particularly alkali metal salts, and specifically includes the reduced form, dihydrolipoic acid. Since lipoic acid is fat- rather than water-soluble, the water-soluble sodium salt is especially useful in embodiments that have an aqueous base. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid.

As mentioned above, lipoic acid is fat-soluble. Therefore, lipoic acid preparations can be applied neat to skin areas subject to damage or already damaged. It is an advantage of the invention that the active compound is fatty so that it physically contributes to the lubrication and soothing of affected skin areas.

However, only effective amounts of lipoic acid are needed to prevent or treat skin damage, so generally topical application to exposed or affected skin sites is accomplished in association with a carrier, and particularly one in which the active ingredient is soluble per se or is effectively solubilized (e.g., as an emulsion or microemulsion). It is necessary that the carrier be inert in the sense of not bringing about a deactivation of the lipoic acid or derivative, and in the sense of not bringing about any adverse effect on the skin areas to which it is applied.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in a carrier will be suitable, requiring only that more frequent topical application be resorted to. As a practical matter, however, to avoid the need for repeated application, it is desirable that the topically applied composition be formulated to contain at least about 0.25% to about 5% by weight, more preferably from about 1% to about 3% by weight, lipoic acid or a derivative thereof, and accordingly, carriers will be chosen which can solubilize or disperse the active ingredients at such concentrations. One efficacious embodiment contains about 2% by weight lipoic acid.

While the carrier for lipoic acid can consist of a relatively simple solvent or dispersant such as oils, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred for skin are those carriers which are fat-soluble, i.e., those which can effectively penetrate skin layers and deliver the active lipoic acid to the lipid-rich layers of the skin.

Many preferred embodiments of this invention contain at least one or two other active ingredients in addition to lipoic acid. It has been observed that lipoic acid had a protective effect on components of a lens antioxidant system comprising ascorbate/dehydroascorbate (Maitra, et al., cited above); the same authors suggested it may be of possible usefulness in the prevention of cataracts. In this invention involving other tissues, fat-soluble fatty acid esters of ascorbic acid (vitamin C) may be added to the lipoic acid composition in some embodiments. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

Tocotrienol may also be added to the lipoic acid composition, alone or in combination with an ascorbyl fatty acid ester in some embodiments. Dihydrolipoic acid has been shown to enhance vitamin E recycling in other systems (ibid.). The term "tocotrienol" encompasses counterparts of tocopherol (vitamin E) that bear unsaturated tails, and include, but not limited to, α-, β-, γ-, and δ-tocotrienols, desmethyl-tocotrienol, didesmethyl-tocotrienol (occurring in sunflower seeds, vegetable oils, barley, brewer's grains, oats, and African violets), their synthetic counterparts, their counterparts having methylated or demethylated chroman rings, and mixtures thereof. The double bonds may be cis or trans or mixtures thereof.

In many embodiments utilizing tocotrienol in the composition, the tocotrienol is isolated from natural sources and added to the formulation as a tocotrienol-enriched vitamine E preparation. However, synthetic preparations may also be employed as well as mixtures of natural and synthetic vitamin E. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, bran, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds.

As with other vitamin E preparations, tocotrienol or tocotrienol-enriched preparations include those containing tocotrienol and, in some cases, tocopherol derivatives, particularly stabilized derivatives. These typically include derivatives related to the phenolic hydroxyl functionality, i.e., wherein it is acylated with an organic acid to form an ester. Examples of such stabilized tocotrienols include, but are not limited to, tocotrienol acetate, tocotrienol succinate, and mixtures thereof. However, the derivatives may also include those involving other reactive groups known to those skilled in the art. Where tocotrienol derivatives are employed, they must be functionally equivalent to tocotrienol. Preferred derivatives contain both the chromanol nucleus and three double bonds in the hydrocarbon tail.

The combination of tocotrienol or tocotrienol-enriched vitamin E preparations and/or a fat-soluble vitamin C fatty acid ester, preferably both, in a dermatologically acceptable carrier with lipoic acid or a derivative is especially advantageous in compositions because lipoic acid augments the efficacy of the other ingredients in the composition. The combination of up to three active ingredients readily solubilizes in the lipid-rich layers of the skin and together scavenge free radicals involved in aging, inflammation, and other skin damage.

The effectiveness of lipoic acid and lipoic acid derivatives, especially when employed in combination with ascorbyl fatty acid esters and/or tocotrienols, can be postulated as resulting from the antioxidant properties of active ingredients per se, which properties are unexpectedly retained and provided to a high degree when used in concert with lipoic acid when these are delivered in combination to the skin in an extremely effective manner in an oil phase. The mechanism of the effect is not well understood, but may be related to the anti-oxidant properties of the active compounds and/or their interference with chemical reactions.

In terms of a possible explanation for the effectiveness of the active ingredients in the prevention or treatment of damage to the skin, it is noted that lipoic acid, as an antioxidant, can scavenge free radicals such as the oxygen radicals created by exposure of skin cells to damage, as well as the generation of free radicals produced by normal metabolism extracellularly and intracellularly. Dihydrolipoic acid, for example, as a powerful antioxidant concentrated in cell membranes, can lessen erythema by the mechanism of free radical scavenging and chain breaking chemical reactions. Ascorbic acid is a powerful reducing agent that can prevent oxidative damage and regenerate chromanoxyl radicals formed as vitamin E derivatives scavenge radicals, reforming vitamin E that can scavenge more radicals. Preferred embodiments of this invention harness this synergestic effect.

In addition, ascorbic acid can increase cyclo-oxygenase activity in human cells. Cyclo-oxygenase is a key enzyme in the oxidation of arachadonic acid, which leads the formation of prostaglandins which in turn mediate inflammation.

Some embodiments further include α-hydroxy acid ingredients such as glycolic acid, hydroxymethylglycolic acid, lactic acid, glucuronic acid, galacturonic acid, gluconic acid, glucoheptonic acid, α-hydroxybutyric acid, α-hydroxyisobutyric acid, α-hydroxyvaleric acid, α-hydroxyisovaleric acid, α-hydroxycaproic acid, α-isocaproic acid, tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric acid or derivatives of hydroxy acids such as pyruvic acid, methyl pyruvate, ethyl pyruvate, isopropyl pyruvate, benzoylformic acid, methyl benzoylformate, and ethyl benzoylformate.

Because cell aging is the result of free radical damage, it is apparent that lipoic acid and its derivatives are also effective in the prevention of cell aging, as are combinations with ascorbic acid fatty acid esters and tocotrienols. All the substances are fat-soluble and disperse within cell membranes, acting as free radical scavengers and neutralizers, and prevent the cross-linking of cell membranes that is seen in the aging process. Once the cell membranes are cross-linked, the permeability of cell membranes increases, causing an inefficient exchange of nutrients and waste products within the cell. The decreased cell permeability results in increased ionic concentration of potassium, which then causes decreased messenger RNA production. The increased ionic concentration also interferes with enzyme activity, as enzymes are very much dependent on ionic concentration for their action.

In addition to decreased production of RNA, there is a marked decrease in the production of protein with aging, and therefore the cell cannot repair itself. The altered cellular membranes prevent removal of waste products in the cell, such as lipofucin, which is a histologic characteristic of all aging cells. Lipoic acid and its derivatives, by preventing free radical damage to cell membranes and preventing decreased permeability to cells, can theoretically prevent aging of the cell by maintaining proper ionic concentration, proper disposal of waste products, and efficient protein and RNA production. Topical application of lipoic acid and its derivatives to skin can thus prevent cell aging, and the effect is pronounced when acting in concert with ascorbyl fatty acid esters and/or tocotrienol.

The method of the present invention is particularly useful for the prevention of skin damage which may result from exposure to ultraviolet radiation, but, based upon the likely mechanism of action, also is useful in general for treatment of any radiation-induced skin damage, particularly that associated with free radical related damage. As such, the topical application of lipoic acid according to the invention can also be effective for chronic administration to prevent the free radical damage seen in the natural aging process of the skin and the free radical damage caused by chronic exposure to sunlight. Lipoic acid, alone or with tocotrienol and/or ascorbyl fatty acid esters can thus be added to dermatological creams and emollients as well as to commercial suncreens to enhance their anti-aging and anti-cancer activity.

It is an advantage of the invention that, because of the efficiency of free radical scavenging and other biochemical mechanisms involved after application of active ingredients to skin, compositions of the invention exhibit efficacy when applied to a variety of skin damaged conditions, including dry skin, psoriasis, and dermatitis (contact, irritant, and allergic). Compositions of the invention can also be used as a treatment after burn.

Generally, the composition is topically applied to the affected skin areas in a predetermined or as-needed regimen to bring about improvement, it generally being the case that gradual improvement is noted with each successive application. Insofar as has been determined based upon clinical studies to date, no adverse side effects are encountered.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all modifications and variations be included within the scope of the invention. The claims are meant to cover the claimed components and steps in any sequence which is effective to meet the objectives there intended, unless the context specifically indicates the contrary.

I claim:

1. A method for treating skin inflamation or aging mediated by free radicals, said method comprising topically applying to skin areas to be treated a composition containing an active compound selected from the group consisting of lipoic acid, lipoic acid esters, lipoic acid amines, salts of lipoic acid, and mixtures thereof, in an amount sufficient to provide free radical scavenging in the skin.

2. A method according to claim 1 wherein the active compound is selected from the group consisting of lipoic acid, dihydrolipoic acid, and mixtures thereof.

3. A method according to claim 2 wherein the composition contains from about 0.25% to about 5% by weight active compound.

4. A method according to claim 1 wherein the composition further comprises a fat-soluble fatty acid ester of ascorbic acid.

5. A method according to claim 4 wherein the fat-soluble fatty acid ester of ascorbic acid is selected from the group consisting of ascorbyl palmitate, ascorbyl laurate, ascorbyl myristate, ascorbyl stearate, and mixtures thereof.

6. A method according to claim 5 wherein the fat-soluble fatty acid ester of ascorbic acid is ascorbyl palmitate.

7. A method according to claim 1 wherein the composition further comprises a tocotrienol.

8. A method according to claim 7 wherein the tocotrienol is selected from the group consisting of α-tocotrienol, β-tocotrienol, γ-tocotrienol, δ-tocotrienol, desmethyl-tocotrienol, didesmethyl-tocotrienol, and mixtures thereof.

9. A method according to claim 3 wherein the composition further comprises a fat-soluble fatty acid ester of ascorbic acid and a tocotrienol.

10. A method for the treatment of skin inflammation or aging mediated by free radicals, said treatment comprising topically applying to the skin to be treated a composition containing, in a dermatologically acceptable carrier, two groups of compounds (a) and (b), wherein (a) is a compound selected from the group consisting of lipoic acid, lipoic acid esters, lipoic acid amides, salts of lipoic acid, dihydrolipoic acid, and mixtures thereof, and (b) is a fat-soluble fatty acid ester of ascorbic acid, in an mount sufficient to provide free radical scavenging in the skin.

11. A method according to claim 10 wherein the lipoic acid or lipoic acid derivative is selected from the group consisting of lipoic acid, dihyrolipoic acid, and mixtures thereof, and the fat-soluble fatty acid ester of ascorbic acid is selected from the group consisting of ascorbyl palmitate, ascorbyl laurate, ascorbyl myristate, ascorbyl stearate, and mixtures thereof.

12. A method according to claim 11 wherein the composition comprises dihydrolipoic acid and ascorbyl palmitate.

13. A method according to claim 11 wherein the composition further comprises a tocotrienol.

14. A method according to claim 11 wherein the composition further comprises an α-hydroxy acid.

15. A method according to claim 14 wherein the α-hydroxy acid is glycolic acid.

* * * * *

UNITED STATES PATENT AND TRADEMARK OFFICE
CERTIFICATE OF CORRECTION

PATENT NO. : 5,709,868
DATED : January 20, 1998
INVENTOR(S) : Nicholas V. Perricone It is certified that error appears in the above-identified patent and that said Letters Patent is hereby corrected as shown below:

<u>Title page,</u>
Item [56], References Cited, FOREIGN PATENT DOCUMENTS, add
-- DE   4,417,038 to C.H. Weischer, 1995 --

Signed and Sealed this

Twenty-third Day of September, 2003

JAMES E. ROGAN
*Director of the United States Patent and Trademark Office*

(12) EX PARTE REEXAMINATION CERTIFICATE (4972nd)
United States Patent
Perricone

(10) Number: US 5,709,868 C1
(45) Certificate Issued: Aug. 10, 2004

(54) LIPOIC ACID IN TOPICAL COMPOSITIONS

(75) Inventor: Nicholas V. Perricone, 27 Coginchaug Ct., Guilford, CT (US) 06437

(73) Assignee: Nicholas V. Perricone, Guilford, CT (US)

Reexamination Request:
No. 90/006,081, Aug. 13, 2001

Reexamination Certificate for:
Patent No.: 5,709,868
Issued: Jan. 20, 1998
Appl. No.: 08/531,290
Filed: Sep. 20, 1995

Certificate of Correction issued Sep. 23, 2003.

(51) Int. Cl.⁷ .............................. A61K 7/48; A61K 7/42
(52) U.S. Cl. ..................... 424/401; 424/59; 424/450; 514/785; 514/863; 514/887; 514/937; 514/944; 514/947; 514/969; 514/440
(58) Field of Search .................... 424/401, 59, 450; 514/785, 863, 887, 937, 944, 947, 969

(56) References Cited

U.S. PATENT DOCUMENTS

| | | | |
|---|---|---|---|
| 4,990,330 A | 2/1991 | Oyama | 424/59 |
| 5,084,481 A | 1/1992 | Ulrich et al. | 514/557 |
| 5,114,716 A | 5/1992 | N'Guyen et al. | 424/401 |
| 5,376,361 A | 12/1994 | Perricone | 424/59 |
| 5,411,991 A | 5/1995 | Shander et al. | 514/665 |
| 5,472,698 A | 12/1995 | Rawlings et al. | 424/401 |
| 5,565,462 A | 10/1996 | Eitan et al. | 514/262 |
| 5,569,670 A | 10/1996 | Weischer et al. | 514/440 |
| 5,607,980 A | 3/1997 | McAtee et al. | 514/476 |
| 5,653,988 A | 8/1997 | Gerber et al. | 424/401 |
| 5,658,556 A | 8/1997 | Gers-Barlag et al. | 424/63 |
| 5,665,364 A | 9/1997 | McAtee et al. | 424/401 |

FOREIGN PATENT DOCUMENTS

| | | |
|---|---|---|
| DE | 43 44 741 | 6/1995 |
| DE | 4417038 | * 11/1995 |
| EP | 0 308 919 | 3/1989 |
| EP | 0 572 922 | 5/1993 |
| JP | 56120611 | 9/1981 |
| JP | 62175415 | 8/1987 |
| WO | WO 95/14466 | 6/1995 |

OTHER PUBLICATIONS

Biothols in Health and Disease, edited by Packer & Cadenas, New York: M Dekker, 1995.

* cited by examiner

*Primary Examiner*—Theodore J. Criares

(57) ABSTRACT

In a method for the prevention and/or treatment of skin damage, particularly inflammation and aging, a composition containing lipoic acid and/or a lipoic acid derivative is topically applied to affected skin areas. A fat-soluble fatty acid ester of ascorbic acid such as palmityl ascorbate and/or tocotrienol is preferably applies with the lipoic acid or derivative in association with a dermatologically acceptable carrier.

1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 38–39:

In one particularly preferred embodiment, the topical composition contains lipoic acid [or dihydrolipoic acid or mixtures thereof], ascorbyl palmitate, and tocotrienol as active ingredients.

Column 2, lines 64–67:

In one embodiment, the composition contains from about 0.25 to about 5 weight %, preferably from about 1% to about 3%, lipoic acid [or dihydrolipoic acid]. In one embodiment, 2% lipoic acid is employed.

AS A RESUT OF REEXAMINATION, IT HAS BEEN DETERMINED THAT:

Claims 1, 2 and 10–12 are determined to be patentable as amended.

Claims 3–9 and 13–15, dependent on an amended claim, are determined to be patentable.

New claim 16 is added and determined to be patentable.

1. A method for treating skin [inflamation or] aging mediated by free radicals, said method comprising topically applying to skin areas to be treated a composition containing an active compound selected from the group consisting of lipoic acid, lipoic acid esters, lipoic acid amines, salts of lipoic acid, and mixtures thereof, in an amount sufficient to provide [free radical scavenging] *protein production* in the skin.

2. A method according to claim 1 wherein the active compound is [selected from the group consisting of] lipoic acid[, dihydrolipoic acid, and mixtures thereof].

10. A method for the treatment of skin [inflammation or] aging mediated by free radicals, said treatment comprising topically applying to the skin to be treated a composition containing, in a dermatologically acceptable carrier, two groups of compounds (a) and (b), wherein (a) is a compound selected from the group consisting of lipoic acid, lipoic acid esters, lipoic acid amides, salts of lipoic acid, [dihydrolipoic acid,] and mixtures thereof, and (b) is a fat-soluble fatty acid ester of ascorbic acid[, in an mount sufficient to provide free radical scavenging in the skin].

11. A method according to claim 10 wherein [the] *compound (a) is* lipoic acid [or lipoic acid derivative is selected from the group consisting of lipoic acid, dihydrolipoic acid, and mixtures thereof], and [the fat-soluble] *compound (b) is* a fatty acid ester of ascorbic acid [is] selected from the group consisting of ascorbyl palmitate, ascorbyl laurate, ascorbyl myristate, ascorbyl stearate, and mixtures thereof.

12. A method according to claim 11 wherein the composition comprises [dihydrolipoic] *lipoic* acid and ascorbyl palmitate.

*16. A method for treating skin aging mediated by free radicals, said method comprising topically applying to skin areas to be treated a composition containing (1) an effective amount of lipoic acid, and (2) an effective amount of one or more of (a) tocotrienols and tocotrienol derivatives and vitamin E compositions enriched with tocotrienols or tocotrienol derivatives; (b) fatty acid esters of ascorbic acid; (c) α-hydroxy acids.*

\* \* \* \* \*